United States Patent [19]
DeCampli

[11] Patent Number: 5,797,879
[45] Date of Patent: Aug. 25, 1998

[54] APPARATUS AND METHODS FOR PROVIDING SELECTIVELY ADJUSTABLE BLOOD FLOW THROUGH A VASCULAR GRAFT

[76] Inventor: William M. DeCampli, 8 Heritage Ct., Atherton, Calif. 94027

[21] Appl. No.: 703,096

[22] Filed: Aug. 26, 1996

[51] Int. Cl.⁶ .................................................. A61M 29/00
[52] U.S. Cl. ............................................ 604/96; 604/98
[58] Field of Search .................. 604/264, 96; 606/191, 606/192, 194, 198

[56] References Cited

U.S. PATENT DOCUMENTS

| | | | |
|---|---|---|---|
| 3,701,345 | 10/1972 | Heilman et al. | 128/2 R |
| 3,730,186 | 5/1973 | Edmunds, Jr. et al. | 128/325 |
| 3,831,583 | 8/1974 | Edmunds, Jr. et al. | 128/1 R |
| 4,006,736 | 2/1977 | Kranys et al. | 128/2 A |
| 4,828,544 | 5/1989 | Lane et al. | 604/9 |
| 4,941,472 | 7/1990 | Moden et al. | 128/419 |
| 5,205,286 | 4/1993 | Soukup et al. | 128/630 |
| 5,284,146 | 2/1994 | Czar et al. | 128/662.03 |
| 5,320,100 | 6/1994 | Herweck et al. | 128/654 |

OTHER PUBLICATIONS

A. Ahmadi, J. Rein, K. Hellberg, C. Bastanier, "Percutaneously Adjustable Pulmonary Artery Band," Supplement to *The Annals of Thoracic Surgery*, vol. 60, No. 6 (Suppl), Dec. 1995.

L. Henry Edmunds, Jr., L.W. Rudy, M.A. Heymann, J.K. Boucher, "An Adjustable Pulmonary Arterial Band," *Trans. Amer. Soc. Artif. Int. Organs*, vol. XVIII, 1972, pp. 217–223.

*Primary Examiner*—Manuel Mendez
*Attorney, Agent, or Firm*—Fish & Neave; Nicola A. Pisano

[57] ABSTRACT

Apparatus for adjusting blood flow through a graft is provided comprising a balloon disposed against the exterior surface of the graft by a substantially rigid sheath, so that when the balloon is inflated with an inflation medium it causes constriction of blood flow through the graft without creating potentially thrombogenic crimps or infolds in the graft material. The balloon is adjusted by connecting an infusion device to a subcutaneously implanted balloon access port. A pair of ultrasonic elements may be optionally provided to measure blood flow through the graft and to optimize the extent of constriction of the graft. Electrical connection between the ultrasonic elements and external ultrasound processing circuitry is established via a subcutaneously implanted electrical access port that enables multiple electrical connections to be made using a single needle stick.

6 Claims, 4 Drawing Sheets

APPARATUS AND METHODS FOR PROVIDING SELECTIVELY ADJUSTABLE BLOOD FLOW THROUGH A VASCULAR GRAFT

BACKGROUND OF THE INVENTION

Children born with certain congenital heart lesions that include obstruction of blood flow to the lungs frequently require that a graft, or "shunt" be placed between the systemic arterial system and the lungs to supply blood to the lungs. The first such operation was performed in 1945 by Alfred Blalock and Helen Taussig using the native left subclavian artery as the graft material. It was a landmark in the treatment of complex congenital heart disease. Since then, prosthetic materials, particularly polytetrafluoroethylene (also known as "PTFE" or Gortex®, a trademark of W. L. Gore & Associates, Inc., Newark, Del., USA, have replaced harvesting of a native artery as the main graft material used for this operation. The operation is performed alone or in combination with other procedures in children from the newborn period to the second decade of life. Such shunts are commonly referred to as "modified Blalock-Taussig shunts."

Despite the current trend toward definitive one stage correction for a variety of congenital cardiac lesions, shunts are still employed in lesions such as tetralogy of Fallot with anomalous coronary anatomy, transposition of the great vessels with ventricular septal defect and left ventricular outflow obstruction, pulmonary atresia with intact ventricular septum, pulmonary atresia with VSD that cannot be closed in one stage, hypoplastic left heart syndrome, complex single ventricle anatomy with pulmonary stenosis, and other lesions in neonates born too small to undergo total one stage correction. Additionally, shunts or "fenestrations" between the systemic venous circuit and the pulmonary venous atrium are now carried out in a substantial fraction of modified Fontan operations performed worldwide.

Together, these anomalies result in the placement of approximately 3000 shunts annually in the United States, and another 3000 worldwide. To install a typical modified Blalock-Taussig shunt, the surgeon exposes the mediastinum (the contents of the middle of the chest between the two lungs) by dividing the sternum. This is the most common access for all heart operations. The pulmonary artery and a major artery (for example, the subclavian artery) are exposed. The distance between them is measured, then a segment of PTFE graft of appropriate diameter is cut to this measured length. The major artery is clamped, and an opening made in the artery. One end of the graft is then sewn to the artery in fluid communication with the opening. The pulmonary artery is then clamped, and an opening made in it. The other end of the graft is then sewn to the pulmonary artery in fluid communication with the opening. The clamps are then released to establish flow in the graft, going from the major artery to the pulmonary artery (and hence to the lungs).

While performing the operation, the surgeon must make a judgment as to how large the diameter of the graft should be to provide adequate blood flow. Unfortunately, the ideal diameter for the graft generally cannot be predicted with any accuracy. If the graft diameter is too small, the patient will become too cyanotic (blue) since he or she will not have adequate oxygen in the bloodstream. Thus, an undersized graft can result in death in certain cases. If, on the other hand, the graft diameter is too large, the heart will pump too much blood through the lungs (i.e., more than is needed), causing the heart to overwork and fail and death can result. In both situations the patient can become unstable soon after operation, and a number of deaths occur each year as a result. Attempts to control a situation of "undercirculation" or "overcirculation" with drugs achieve only modest success.

Periodically, the surgeon must exchange the graft for one of a different diameter, usually in an emergency situation requiring a sternotomy in the Intensive Care Unit because there is insufficient time to reach an operating room. Every year there are such instances in which the patient does not survive this intervention. Even if the patient survives the early post-operative course, the shunt flow can become inappropriate at a later time, perhaps weeks later, causing heart failure. Additionally, as the patient grows, the shunt flow can become inadequate for the patient's size. On average, a Blalock-Taussig shunt is used for a period of days to weeks, and is typically removed at the child's definitive operation, which usually occurs within the first twelve to eighteen months of the child's life.

In another clinical situation, that of the child with a single ventricle, an operation called a "modified Fontan" is performed, in which a conduit is placed between the inferior vena cava and the pulmonary artery. Because the hemodynamic response to this operation is somewhat unpredictable, the surgeon frequently places a secondary shunt between the conduit and the common atrial chamber. This shunt is often created using polytetrafluoroethylene material, such as Gortex®, and hence resembles the modified Blalock-Taussig graft. It is frequently desirable to regulate the flow through this graft, and eventually totally occlude it.

In accordance with previously known methods, the shunt used in the modified Fontan technique has been partially occluded by snaring the shunt with heavy suture material either brought out through the skin, or buried just beneath the skin. In the latter case, when the surgeon wishes to regulate the flow, he incises the skin in a reoperation in which the snare is exposed, and tightens down on the snare, thus occluding the graft. This procedure requires a reoperation each time the flow needs adjustment and is expensive, risky and labor intensive.

The morbidity and cost of the current imprecision in regulating shunt flow in infants is considerable. In a recent case involving an institution where approximately 580 pediatric cardiac cases are performed per year, 10 procedures in which shunts were used or considered for use were performed during a three month period. In three cases emergency reoperations were required in the intensive care unit while attempting to save the patient by creating or adjusting shunt flow. In three other cases, multi-organ failure and hemodynamic instability were caused by inappropriate shunt flow.

This experience, in which significant morbidity and cost attended 60% of shunt-related procedures, highlights the absence in the field of apparatus and methods for conveniently and accurately adjusting shunt flow. Currently, there are no known "minimally invasive" techniques (i.e., that avoid the necessity of reoperation) for adjusting blood flow through these types of shunts.

Devices are known for regulating the flow of blood within native arteries and fistulas. For example, Edmunds et al. U.S. Pat. No. 3,730,186 describes an implantable pulmonary artery band including an toroidal balloon occluder that is disposed around the native pulmonary artery. The balloon occluder is inflated via a subcutaneously implanted injection button using a conventional hypodermic needle.

A drawback of the Edmunds et al. device is the lack of a mechanism to accurately determine the degree of constriction caused by the balloon occluder. Moreover, the toroidal shape of the balloon occluder is believed to create crimps or infolds in the arterial wall even at low degrees of constriction. Such crimps or infolds, which project into the flow field of the artery, are expected to disrupt laminar flow within the artery and serve as thrombogenic sites.

Lane et al. U.S. Pat. No. 4,828,544, shows a blood control device having a balloon mounted on a strap which is fastened around a fistula. The interior of the balloon is coupled to a pump which is implanted within the patient along with the strap and balloon. Actuating the pump inflates the balloon and restricts the flow of blood through the fistula.

A significant drawback of the device described in the patent to Lane et al. is that it does not permit accurate determination of the degree of constriction introduced in the fistula, nor can it provide real-time measurement of the flow of blood through the fistula.

In view of the foregoing, it would be desirable to provide implantable apparatus for selectively restricting blood flow through a vascular graft, so as to provide precise control over the amount of blood flow through the graft. It further would be desirable to provide methods and apparatus adapted for connection to the implantable apparatus to provide precise real-time external measurement and control over the implantable apparatus. It also would be desirable to provide implantable apparatus that permits constriction of a vascular graft without infolding or crimping of the graft material, thereby reducing the potential for the development of turbulent flow.

Subcutaneous ports are known that provide vascular access for patients needing chronic intravenous drug administration, such as antibiotics, chemotherapy, or blood transfusions. Such ports are made by several companies, for example, the Infuse-A-Port™ and DualPort™ products made by Infusaid, Inc., Norwood, Mass., USA, and the Hickman ports made by Davol, Inc., Cranston, R.I., USA. The lowest profile port is the CathLink® 20 by Bard Access Systems, Salt Lake City, Utah, USA.

Access ports permitting electrical connection to an implantable device are also known. For example, Soukup et al. U.S. Pat. No. 5,205,286 and Moden et al. U.S. Pat. No. 4,941,472 show subcutaneous implants having a plurality of electrical access ports. Each access port accepts a single electrical connection. A drawback of the devices described in the foregoing patents is that a separate needle and needle stick is required for each electrical connection, thus increasing patient discomfort and the risk of infection.

SUMMARY OF THE INVENTION

In view of these and other limitations and disadvantages of previously known devices, it is an object of the present invention to provide an implantable apparatus that selectively regulates blood flow through a vascular graft without requiring reoperation.

It is a further object of the present invention to methods and apparatus that permit optimization of oxygenation and preload to the heart of a patient having a synthetic graft.

It is another object of the present invention to provide apparatus for precisely measuring the blood flow through a vascular graft in real-time.

It is a yet further object of the invention to provide apparatus for constricting a vascular graft in-situ that reduces the potential for crimping or infolding of the graft material, thus reducing the potential for the development of turbulent zones or stagnation points within the flow field of the vascular graft.

It is still another object of the present invention to provide implantable apparatus for measuring blood flow through a graft, which implantable apparatus may be connected to external signal processing apparatus using only a single needle stick.

It is a yet further object of the present invention to provide an electrical access port which is practical, safe, and comfortable for the patient.

It is a still further object of the present invention to provide an implantable electrical access port and needle that provides multiple electrical connections with a single needle stick.

The above and other objects of the present invention preferably are accomplished by providing an implantable apparatus comprising a selectively inflatable balloon and a sheath for enclosing the balloon against an exterior surface of a vascular graft. The balloon is disposed between the graft and the sheath so that when the balloon is inflated with an inflation medium, it causes constriction of the cross-sectional area of the graft without crimping or infolding, thereby reducing blood flow through the graft while avoiding the creation of potentially thrombogenic sites. The balloon is maintained in an inflated condition. Optionally, an elastically deformable member may be disposed between the graft and the balloon to further reduce the development of turbulence in the flow within the graft at greater degrees of constriction by altering the shape of the deformation caused by balloon inflation.

A substantially non-distensible lumen is disposed in fluid communication with the interior of the balloon and a balloon access port. The balloon access port preferably is implanted subcutaneously within the patient. A non-coring needle is used to infuse inflation medium into the balloon via the balloon access port, using a precision infusion device that allows precise control of the amount of inflation medium introduced into the balloon.

In an alternative embodiment, a plastically deformable tubular member may be disposed between the balloon and the exterior surface of the graft to maintain the graft at a constricted diameter after the balloon has been deflated.

In accordance with another feature of the present invention, the sheath surrounding the balloon and vascular graft may in addition have a plurality of piezoelectric elements disposed in opposition across the cross-section of the graft to serve as ultrasound transducers. The piezoelectric elements thus provide an ultrasound signal that can be correlated with blood flow through the graft. In this embodiment of the implantable apparatus of the present invention, the non-distensible lumen preferably includes wires that electrically couple the piezoelectric elements to an electrical access port. The electrical access port, also preferably implanted subcutaneously, enables the piezoelectric elements to be connected to suitable ultrasound activation and signal processing circuitry.

The electrical access port comprises a body having a chamber and a septum extending across an aperture in the chamber. A plurality of conductors are disposed resiliently in the chamber to receive a corresponding plurality of conductors disposed circumferentially on the shaft of a needle. The conductors on the needle are coupled to suitable circuitry for activating the piezoelectric elements to generate ultrasound signals and to receive those signals and process them, thereby enabling a physician to monitor the rate of blood flow through the graft.

Methods are also provided for selectively adjusting the flow through a graft, and for measuring the flow through the graft, using the above-described apparatus.

BRIEF DESCRIPTION OF THE DRAWINGS

Further features of the invention, its nature and various advantages, will be more apparent upon consideration of the following detailed description, taken in conjunction with the accompanying drawings, in which.

DETAILED DESCRIPTION OF THE INVENTION

Figure 1:
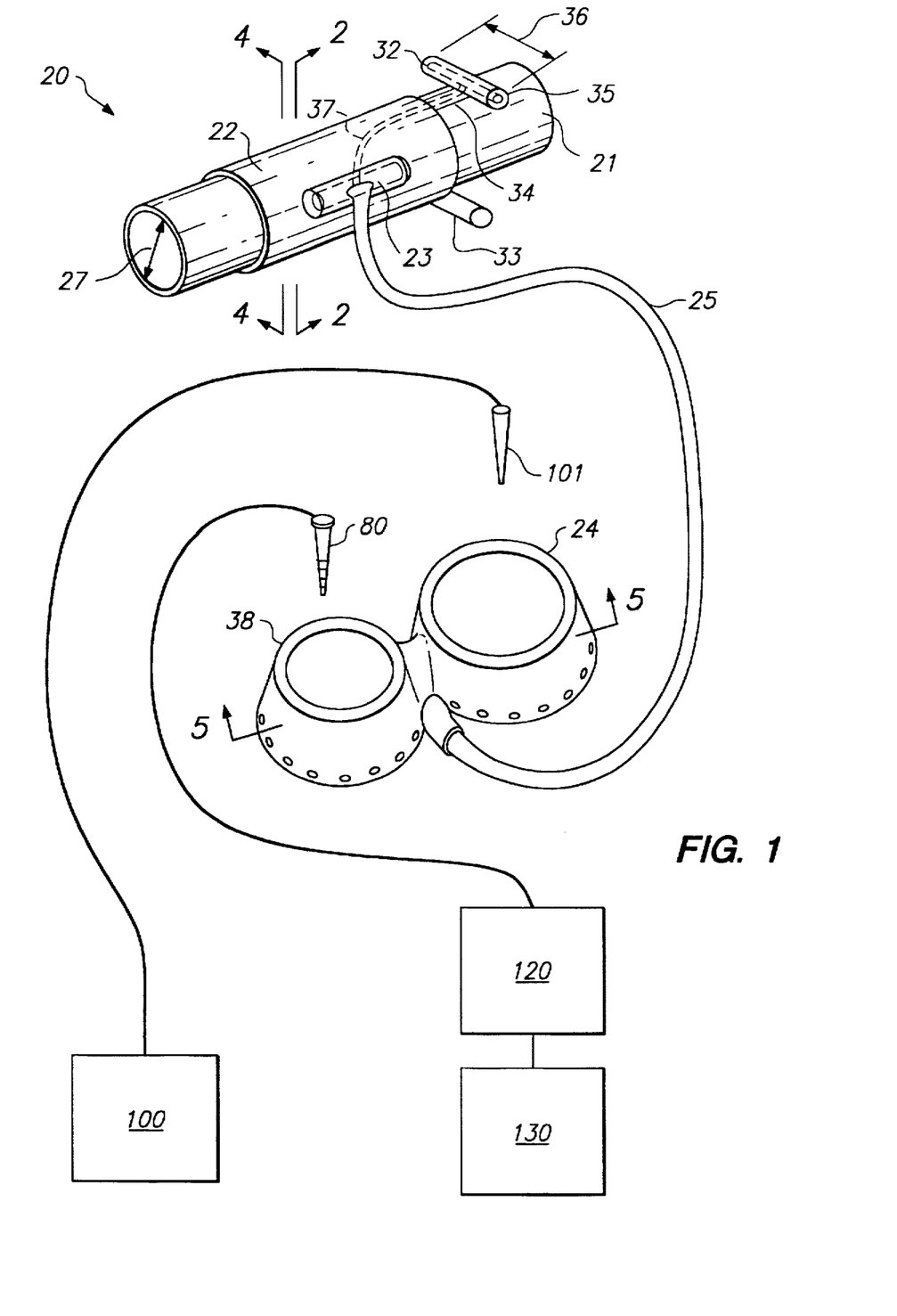
FIG. 1 is a view, partly perspective and partly schematic, of apparatus constructed in accordance with the principles of the present invention.
Figure 2:
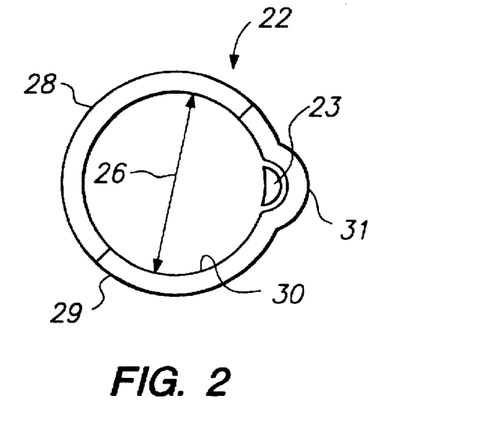
FIG. 2 is a cross-section of the sheath and balloon of FIG. 1 taken along view line 2—2.
Figure 3:
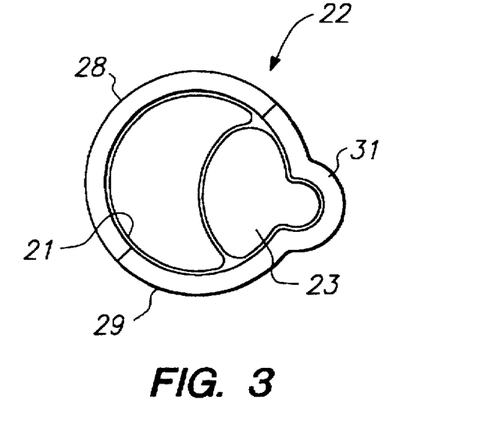
FIG. 3 is a cross section of the apparatus of FIG. 1 taken along view line 2—2 showing the balloon partly inflated.

Referring to FIGS. 1-3, an illustrative embodiment of apparatus 20 for providing an adjustable flow through a vascular graft, constructed in accordance with the present invention, is described. Apparatus 20 comprises a flexible vascular graft 21 enclosed within sheath 22 with selectively inflatable balloon 23, balloon access port 24 and substantially non-distensible connecting lumen 25. Infusion device 100 injects and withdraws an inflation medium through balloon access port 24 using needle 101, thereby providing a controlled degree of expansion of balloon 23. Apparatus 20 may optionally include a pair of ultrasonic elements that may be coupled via an electrical access port to ultrasound driving circuitry 120 and processing circuitry 130, as described in detail hereinafter.

In accordance with the principles of the present invention, inflation of balloon 23 causes vascular graft 21 to become constricted substantially without crimping or forming infolds that project into the flow field within the graft. This feature of the present invention is expected to reduce the likelihood of creating potentially thrombogenic sites caused by turbulent flow over the crimped or infolded graft material, or from stagnation points within the flow field.

Graft 21 comprises a fluid impermeable material, such as polytetrafluoroethylene (PTFE) or a polyester fabric such as Dacron®, a trademark of E. I. Du Pont de Nemours, Wilmington, Del., USA. Graft 21 may optionally include an external winding of a resilient plastic, thereby enhancing elastic recoil of the graft after balloon 23 has been deflated. Graft 21 is of sufficient length to connect two arteries and of sufficient diameter to provide a range of appropriate constricted diameters in an intended application. Thus, for example, in a typical Blalock-Taussig shunt, the length of graft 21 may be about 20 mm, while a suitable unconstricted diameter may be about 5 mm. As will of course be understood, the size of graft 21 depends upon the size of the patient, and the dimensions of apparatus 20 are preferably tailored to meet the functional requirements of the particular surgical application.

Sheath 22 preferably is made of plastic (e.g., polyethylene) having sufficient rigidity to experience little diametral expansion when balloon is inflated to constrict vascular graft 21. Applicant expects that this requirement may be achieved using a sheath having a thickness of between about 0.3 mm and 1.0 mm, depending upon the material selected. Sheath 22 preferably is approximately circular in cross-section and of a length so that the ends sheath 22 do not impinge upon the suture lines at each end of the graft (where the graft is connected to the native vasculature). The cross-sectional deformation of the sheath should accommodate deformation of the graft during balloon inflation, for example, to take on an elliptical shape to some extent, so as to minimize the amount of space between graft 21 and sheath 22, or between sheath 22 and a deformable member (described hereinbelow). For example, for a vascular graft about 20 mm long, applicant expects that the sheath should extend over approximately the center 10 mm of the graft.

Sheath 22 may be constructed as two half-circumferences 28 and 29, which may be fastened together to enclose balloon 23 against graft 21 using suitable biocompatible fastening means, for example, one or more grommets, clips or hooks. In one embodiment, interior diameter 26 of sheath 22 is about equal to exterior diameter 27 of graft 21, so that interior surface 30 of sheath 22 lies nearly flush with the exterior of graft 21, thereby reducing tissue ingrowth between the sheath and the graft.

In an alternative embodiment, an elastically deformable member may be interposed between graft 21 and sheath 22, preferably surrounding graft 21. The elastically deformable member is constructed to alter the shape of the deformation of the graft so as to further reduce the development of flow stagnation points and the development of turbulent flow areas in the flow field when the graft is highly constricted. The elastically deformable member also serves to restore graft 21 to a larger diameter when balloon 23 is deflated. In this case, sheath 22 preferably has an approximately elliptical shape and may be somewhat deformable to accommodate deformation of the elastically deformable member, while minimizing space between the elastically deformable member and sheath 22 to reduce tissue ingrowth.

To further reduce tissue ingrowth, which might interfere with operation of apparatus 20, graft 21 and sheath 22 (including the elastically deformable tube, if present) may be sealed together. For example, the ends of sheath 23 may be sealed to the exterior of graft 21 using a thin drape or wrap of substantially non-porous biocompatible material, such as PTFE or a silicon-based film, that extends nearly the entire length of the graft. Alternatively, graft 21, sheath 22 and balloon 23 may be provided preassembled (and in a range of sizes) in suitable sterile packaging directly from a manufacturer. Applicant expects that a drape of ultra-low porosity PTFE having an internodal distance of about 10 μm will provide satisfactory protection.

Referring still to FIGS. 1–3, sheath 22 may include raised tube-like portion 31 arranged parallel to longitudinal axis of the sheath to accommodate balloon 23 in its deflated condition. Raised portion 31 preferably is about 5.0 mm in length and about 1.0 mm in diameter, and preferably is open along its length to the inside lumen of the sheath. In general, raised portion 31 is shaped so that, when deflated, balloon 23 fits within the raised portion and is flush with the interior surface 30 of sheath 22. Raised portion 31 may include an aperture near its mid-length having a diameter between about 0.5 mm and about 1.0 mm through which connecting lumen 25 is coupled to provide fluid communication between balloon 23 and connecting lumen 25. Alternatively, connecting lumen 25 may be coupled to balloon 23 at either end.

Balloon 23 is made of materials commonly used in balloon catheters, such as polyethylene, nylon, or similar suitable material, and is substantially more compliant than sheath 22, so that expansion of balloon 23 cause constriction of graft 21, rather than diametral expansion of sheath 22. Balloon 23 may be attached along its length to the interior surface of raised portion 31 of sheath 22 using conventional fixation techniques. Balloon 23 is preferably cylindrically shaped using techniques which are per se known for instilling "memory" in balloon material during manufacturing, for example, using conventional biaxial orientation techniques. Balloon 23 should have a diameter selected to achieve a maximum desired degree of constriction of graft 21 when the balloon is inflated to its maximum diameter. For example, the illustrative balloon shown in FIGS. 1–3 may have a maximum inflation diameter of about 6.0 mm and a length of about 6.0 mm. It will of course be understood, however, that because balloon 23 and sheath 22 may have to be employed with a graft considerably shorter than 20 mm, balloons of other shapes and sizes may be used, for example, a balloon may have a maximum circumference of 5 to 6 mm, but a length of only 3 mm, so long as substantially no crimping or infolding of the graft material results during balloon inflation.

The compliance of the balloon preferably is such that the inflation pressure does not exceed a so-called "functional value," determined by considering the following three factors: (1) the pressure needed to deform the graft when blood is flowing through it; (2) the desire to have minimal distortion of balloon shape during graft deformation; and (3) the desire to stay within the functional value at which all pressurized components (balloon, connecting lumen, port and all connections) are leakproof for the desired period of inflation (which may vary from days to months, depending on the clinical application). The functional value for most applications is expected to be between about 2 and 3 atmospheres. Such pressures are commonly achieved in previously known embolectomy catheter balloons.

The composition and thickness of the balloon material is such that it is essentially leakproof for the selected inflation medium for periods ranging from days to months, depending upon the clinical application. The burst pressure of the balloon material preferably is several times the functional value (i.e., higher than that which might be accidentally achieved during inadvertent aggressive infusion). Balloon 23 preferably does not significantly plastically deform or experience significant creep deformation at its working pressure and over the expected extended periods of inflation.

The inflation medium preferably also may be evacuated from the balloon after an extended period of inflation ranging from days to months, depending on the clinical application.

The inflation medium should be selected to be chemically compatible with the components of the system, for example, saline or glycerine. While an inert gas may also be used and has the advantage of having a low reactivity, it is expected that a gas may have a greater tendency to leak.

As balloon 23 is inflated with the inflation medium, it expands so as to smoothly compress graft 21 without producing kinks, crimps or infolds in either graft 21 or balloon 23. Graft 21 takes on a fishmouth-shaped cross section that progressively narrows with balloon inflation, as shown in FIG. 3. This deformed shape is expected to maintain laminar flow up to quite small cross-sections. As will of course be understood, laminar flow is preferable to turbulent flow, as the latter may result in high shear areas which are conducive to pseudointimal hyperplasia, or buildup of material on the inside surface of the graft. In addition, a regular cross-section is preferable to an irregular one, since the later can result in complex flow patterns with stagnation points that are conducive to platelet adherence and thrombosis. Slight modifications in the shape of raised portion 31 of sheath 22 and/or the shape of balloon 23 may be preferred in some applications to optimize the graft blood flow characteristics.

Figure 3A:
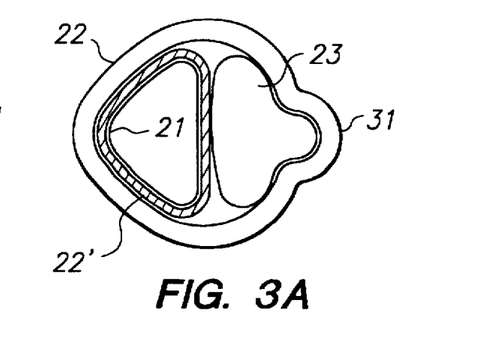
FIG. 3A is a cross section view similar to FIG. 3 showing an alternative embodiment of the apparatus of FIG. 1, wherein an elastically deformable member is interposed between the graft and the balloon.

In an embodiment including an elastically deformable support member surrounding the graft and interposed between the graft and the balloon, inflation of the balloon causes the elastically deformable member to deform to a shape characteristic of that member. For example, such a graft may have a circular shape when the balloon is deflated, but as shown in FIG. 3A. may adopt an elliptical or multi-lobe configuration when the balloon is inflated. As will of course be understood, the deformed configuration of the elastically deformable member 22' should be selected to maintain laminar flow throughout the cross-section of the graft, without stagnation points, even at the highest degree of constriction of the graft.

An estimate of the length scale of geometric irregularities that would cause turbulence corresponds to the Reynolds number, Re, for flow through the graft, and is computed as:

$$Re = v * L * \rho / \mu \qquad (1)$$

where:

v=mean velocity;

L=length scale over which geometry varies;

ρ=density of blood; and

μ=dynamic viscosity of blood.

For a neonate with a cardiac output of about 600 ml/min, the Reynolds number is approximately 33. With no graft deformity, assuming L=4.0 mm, the flow is laminar. However, turbulence might be seen when L approaches 1.0 mm, which might be the case near the corners of the fish mouth seen in FIG. 3. Accordingly, applicant expects that the use of an elastically deformable member as shown in FIG. 3A will provide laminar flow even at high degrees of constriction of the graft.

Connecting lumen 25 includes a passageway to transport the inflation medium from balloon access port 24 to balloon 23 and may include an additional passageway for accommodating a plurality of conducting elements to transmit signals to and from the ultrasonic elements, as described herein below. The length of connecting lumen 25 depends upon the distance from sheath 22 to the subcutaneous site of balloon access port 24 and the size of the patient. Generally, in infants, the port site preferably is subrectus and preperitoneal (behind the rectus muscle, which is an abdominal muscle), while in older children the site preferably is subclavicular. As will be recognized, these sites are commonly used for pacemaker generators and venous access ports.

Connecting lumen 25 comprises a substantially nondistensible material, i.e., one having a very low compliance. The fluid passageway through connecting lumen 25 preferably has an inner diameter between about 2 Fr. and about 4 Fr. As will be readily understood, the use of a substantially non-distensible material is required so that the connecting lumen does not "absorb" inflation medium volumes comparable to the balloon volume at working pressures. In addition, connecting lumen 25 should not plastically deform or experience significant creep deformation over periods of time from days up to months. Likewise, the connections between connecting lumen 25, sheath 22 and access port 24 should not leak over the expected extended periods of inflation.

Referring still to FIGS. 1–3, the flow measurement features of the present invention are now described. Two ultrasonic elements 32 and 33 are disposed in opposition across graft 21 and electrically coupled to circuitries 120 and 130 to provide signals indicative of the rate of blood flow through the graft.

Figure 4:
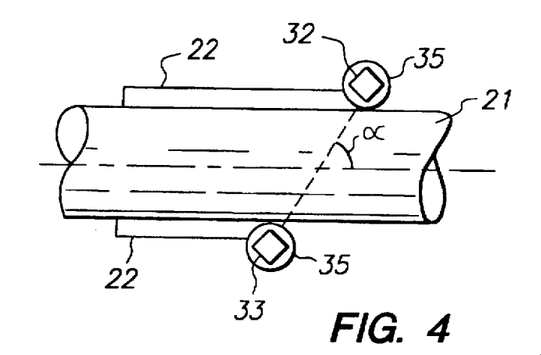
FIG. 4 is a longitudinal cross-sectional fragmentary view of the ultrasonic element portion of the apparatus of FIG. 1, taken along view line 4—4.

Sheath 22 preferably includes an extended portion 34 that provides an arm upon which ultrasonic element 32 is mounted, while ultrasonic element 33 is mounted in opposition to, but preferably axially offset from, ultrasonic element 32. Elongated compartment 35 is affixed to the end of extended portion 34 to house ultrasonic element 32; ultrasonic element 33 is housed in a similar compartment affixed to sheath 22. The compartments housing ultrasonic elements 32 and 33 are smoothly-shaped so that they do not erode the surrounding tissue. Elongated compartment 35 preferably has dimensions of about 6.6 mm by about 3.0 mm, with the longer dimension being perpendicular to the longitudinal axis of graft 21. Although this angle maximizes the accuracy of the transit-time ultrasonic flow measurement, it is not essential, and may not be achievable for grafts having a relatively small ratio of length to width.

Figure 6:
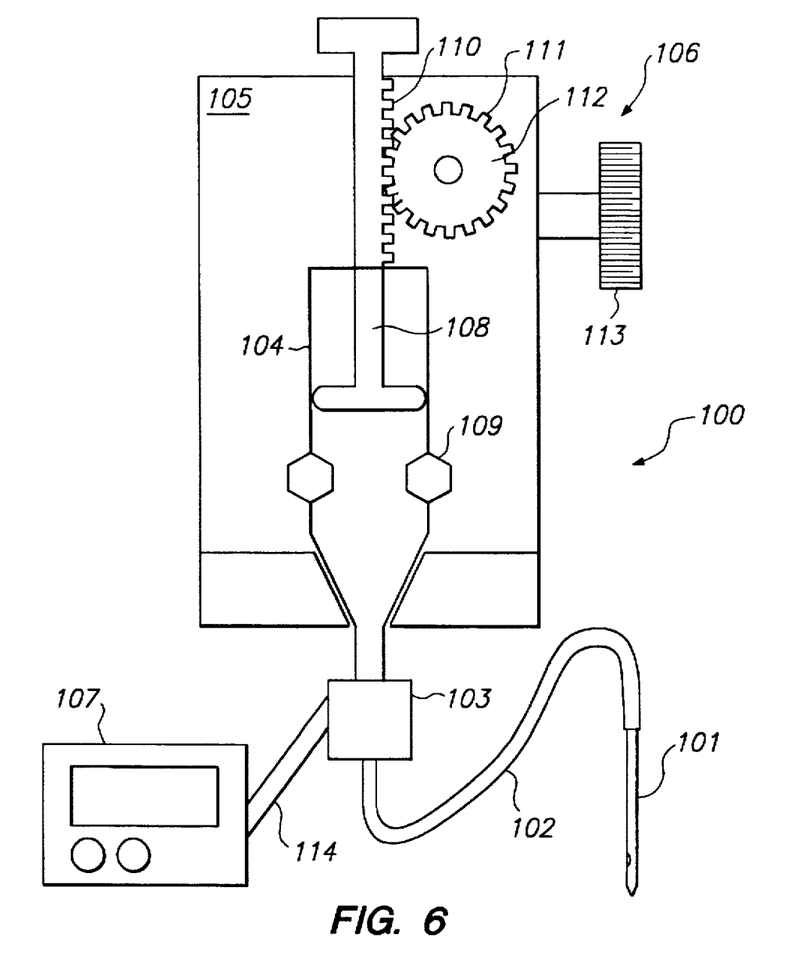
FIG. 6 is a top view of an infusion device or use with the dual access port of FIG. 5.

Ultrasonic elements 32 and 33 preferably are piezoelectric elements capable of generating an approximately planar acoustic wave. Suitable piezoelectric elements may be comprise, for example, a series of layers including a piezoelectric material, such as copolymers of vinylidene fluoride (VDF) and trifluoroethylene (TrFE), for example, available from Toray Industries, Kamakura, Japan. Use of such materials to form ultrasonic transducers is described in Ohigashi et al., "Piezoelectric and Ferroelectric Properties of P(VDF-TrFE) Copolymers And Their Application To Ultrasonic Transducers", page 189 et seq., in *MEDICAL APPLICATIONS OF PIEZOELECTRIC POLYMERS* (Galetti et al. editors), Gordon and Breach Science Publishers S.A. (1988), which is incorporated herein by reference. Length 36 of the ultrasonic elements are preferably greater than diameter 27 of graft 21. As illustrated in FIG. 6, extended portion 34 preferably is dimensioned so that the plane between the faces of ultrasonic elements 32 and 33 form an angle α of about 60° relative to the longitudinal axis of graft 21.

A pair of thin conducting wires 37, preferably molded within the thickness of sheath 22, connect the ultrasonic elements to conductive wires within connecting lumen 25 and to electrical access port 38. The wires preferably emanate from sheath 22 at the site at which connecting lumen 25 is attached and are electrically coupled to corresponding wires extending within a passageway (or attached externally) to connecting lumen 25.

The ultrasonic elements preferably are connected to signal generator 120 via electronic access port 38. The signal generator preferably generates a signal inducing the piezoelectric elements to emit a frequency between about 1.8 MHZ and about 3.6 MHZ, depending on the geometry of the elements. The signal preferably causes an approximately planar wave to be generated, which is transmitted by element 32 and received by element 33 after passing through the blood flowing through graft 21. The received signal is provided to processing circuitry 130 by signal generator 120 via the conductive leads associated with connecting lumen 25 and electrical access port 38. The processor preferably uses the principle of transit time volumetric flow determination to calculate the instantaneous total flow through the graft. This principle, described, for example, in Drost, C. J., "Vessel Diameter-Independent Volume Flow Measurements Using Ultrasound," Proc. of San Diego Biomed. Symp., San Diego, Calif.; San Diego Biomed. Soc., Vol. 17, pp. 299–302 (1978) and U.S. Pat. No. 4,222,407, which are incorporated herein by reference, is used in contemporary volumetric flowmeters for research and clinical use, and is considered superior to Doppler techniques, which are flow geometry dependent.

Applicant expects that a flow resolution of about 2 ml/min can be achieved with the apparatus of the present invention, with a maximum resolved flow of about 5 ml/min and a zero offset of about +15 ml/min, thus providing absolute and relative accuracies of about +15 and +2 percent, respectively. Clinical situations typically require a relative accuracy of approximately +5 percent.

One notable problem with expanded PTFE graft material is that air may become trapped in the interstices of the graft material, which may scatter the acoustic signal generated by the ultrasonic elements. It has been suggested that this effect may be reduced by pre-treating the graft material with a suitable solvent that can penetrate the interstices of the expended PTFE, for example, ethanol, or by lowering the acoustic frequency of the ultrasonic elements, so long as the flow rates through the graft are in a range of 500 to 2000 cc/min.

Figure 5:
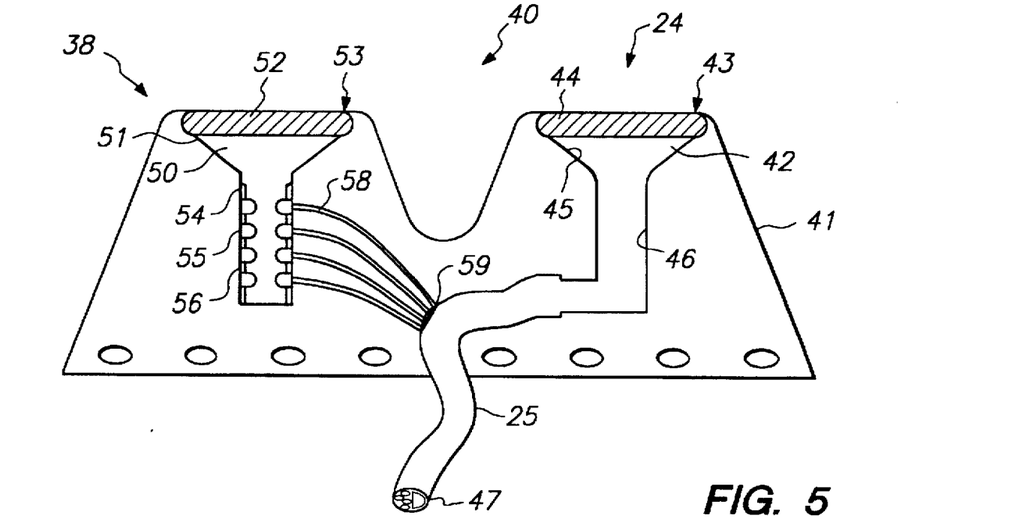
FIG. 5 is a cross-sectional view of the dual access port portion of the apparatus of FIG. 1, taken along view line 5—5.

In the illustrative embodiment of FIG. 1, balloon access port 24 and electrical access port 38 are combined into dual access port 40. As will of course be understood, whether ports 24 and 38 are combined into a single port depends upon the intended application of the apparatus. Referring now to FIG. 5, dual access port 40 is described in greater detail. Dual access port 40 has body 41 which preferably is made of polyethersulfone. Polyethersulfone is lighter than titanium (which is commonly used in subcutaneous port bodies), and is compatible with Magnetic Resonance Imaging scanning.

The balloon access port portion of dual access port 40 includes chamber 42 having aperture 43 covered by septum 44. Septum 44 preferably is made of compressed liquid silicon, so that the septum will not leak even after repeated punctures. Smooth, cone-shaped portion 45 tapers from aperture 43 to lumen 46. Passageway 47 couples lumen 46 to connecting lumen 25.

Referring now to FIG. 6, infusion device 100 for injecting and withdrawing inflation medium into the balloon access port is described. Infusion device 100 comprises needle 101 coupled to substantially non-distensible tubing 102, three-way port 103, syringe 104, removably mounted on support member 105, precision metering system 106, and pressure monitor 107. Syringe 104, needle 101, three-way port 103 and tubing 102 preferably are used only once and disposed, while precision metering system 106 and pressure monitor 107 are reusable.

Needle 101 is preferably non-coring, i.e., the needle will not bore out a piece of septum 44 when inserted into balloon access port 24, and preferably is in a range of 21 to 23 gauge. After needle 101 is inserted into lumen 46 through septum 44, plunger 108 disposed in syringe 104 is moved proximally or distally to inject (or withdraw) inflation medium into (or from) balloon access port 24 through needle 101. To achieve precise infusion volumes, the volume of syringe 104 preferably is between about 0.5 ml and about 0.75 ml.

Support member 105 of infusion device 100 may include a spring-action holder 109 for holding syringe 104 securely in place on support member 105. In operation, syringe 104 is filled to an appropriate level with inflation medium and secured in holder 109. Serrations 110 on plunger 108 are then engaged with teeth 111 of gear 112. Gear 112 forms part of precision metering system 106 and is mechanically coupled to calibrated dial 113. The coupling ratio between dial 113 and gear 112 preferably is such that manual rotation of dial 113 allows precise control over the amount of inflation medium injected into, or withdrawn from, balloon 23 via balloon access port 24.

Gear 112 preferably ratchets, to prevent it from inadvertently rotating in the wrong direction. This feature ensures that transient pressure fluctuations induced in chamber 42 do not cause inflation medium to be pushed back into the syringe. The ratcheting capability of gear 112 may in addition be reversed to allow rotation of the dial in the reverse direction to withdraw inflation medium from the balloon access port, thereby reducing the balloon volume.

Three way port 103 is attached to the proximal end of syringe 104. A short length of low compliance tubing 114 connects an outlet of the three-way port to pressure transducer 107. Pressure transducer 107 continuously measures and displays the pressure in the hydraulic circuit comprising syringe 104, tubing 102, balloon access port 24, connecting lumen 25 and balloon 23.

Infusion device 100 permits the precise inflation of the balloon, and is preferable over standard thumb-action plungers, which applicant expects to be imprecise for use in practicing the invention, since they may allow a slight return of inflation medium into the syringe as a result of access port chamber pressure fluctuations. Thus, although not preferred, it is expected that thumb-action plungers may be successfully used in certain applications of the present invention.

Referring again to FIG. 5, dual access port 40 also includes a portion housing an electrical access port having chamber 50. Chamber 50 has smooth, cone-shaped portion 51 that narrows in diameter from top to bottom along its length. Septum 52, formed from a self-sealing material, such as compressed liquid silicone, extends across aperture 53 in chamber 50. The thickness and resilience of septum 52 preferably are such that, after roughly a dozen non-coring needle punctures, it remains leakproof for periods ranging from days up to months (depending on clinical application).

The diameter of septum 52 and volume of chamber 50 preferably are small, so that the port has a low profile. Thus, for example, chamber 50 may define a volume of about 0.1 ml, and is approximately 10 mm in height, with narrowed portion 51 narrowing from a diameter of about 7.0 mm to about 2.0 mm over a distance of about 2.0 mm. Septum 52 preferably is about 7.0 mm in diameter and about 2.0 mm thick.

Chamber 50 preferably has lumen 54 containing a plurality of resiliently biased electrical contacts 55. Spacing between individual ones of the plurality of electrical contacts 55 provide electrical insulation between adjacent contacts. In the exemplary embodiment shown in FIG. 5, chamber 50 preferably has a length of about 6.0 mm, while each electrical contact 55 is about 0.5 mm wide and separated by a distance between about 0.5 mm and about 1.0 mm from neighboring contacts.

Figure 7:
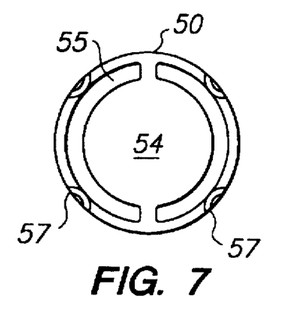
FIGS. 7 through 9 provide top sectional views of illustrative alternative embodiments of the electrical contacts employed in the dual access port of FIG. 5.

Referring now to FIG. 7, electrical contacts 55 may take the form of semi-circumferential rings that are biased toward the center of lumen 54 by springs 57. Springs 57 may be made of metal or plastic, and may constitute small coils rather than U-shaped strips as shown as shown in FIG. 7. Electrical contacts 55 narrow the diameter of the lumen so that, when a small gauge needle (e.g., 22 gauge) constructed in accordance with the present invention is inserted therein, electrical contacts 55 engage mating contacts on the needle.

Figure 8:
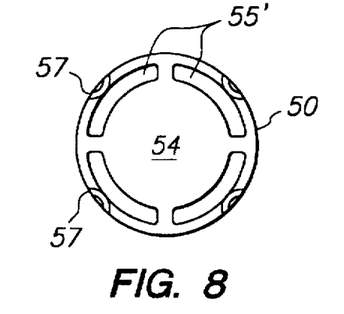
Figure 9:
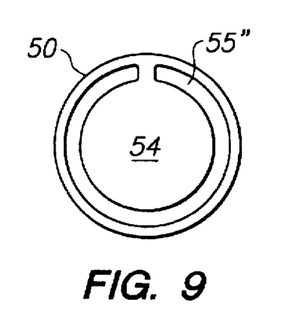

As will be clear to those skilled in the art, electrical contacts other than the two semi-circumferences shown in FIG. 7 may be used in accordance with the present invention. For example, electrical contacts 55 could comprise four quarter-circumferences 55' shown in FIG. 8, or a split ring 55" shown in FIG. 9. The split ring embodiment of FIG. 9 has the added advantage that the spring action is provided by the resilience of the ring itself, thus obviating the need to provide a spring for each electrical contact.

Referring again to FIG. 5, conducting wires 58 are attached to electrical contacts 55 and coalesce at egress site 59 of dual access port 40. Conducting wires 58 are enclosed at the exit of dual access port 40 within connecting lumen 25 so that there is continuous insulation from the surrounding tissue.

Septum 52 electrically isolates the electrical contacts disposed within chamber 50 from the environment, prevents leakage of body fluid into the chamber, and wipes all fluid and tissue from the needle (described herein below) that is inserted into chamber 50 to establish electrical connection between the ultrasonic elements and the external circuitries 120 and 130. To facilitate this wiping function, septum 52 preferably is impregnated or coated with a hydrophilic substance.

Dual access port 40 preferably is silicone encapsulated and includes a plurality of suture holes located around its base for anchoring body 41 to the subcutaneous fascia. The distance between the bottom of chamber 50 and the bottom of body 41 preferably is about 2.0 mm. The diameter of the base of body 41 preferably is about twice the diameter of the septa diameters 44 and 52, so that dual access port 40 remains with its septa facing outward in vivo. Those skilled in the art will appreciate that the shape of dual access port 40 may be varied in accordance with the intended implantation site.

Figure 10:
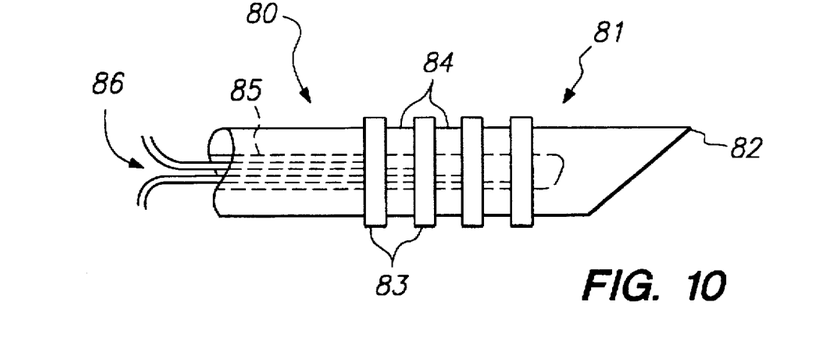
FIG. 10 is side view of the distal end of a needle for use with the electrical access port portion of the dual access port of FIG. 5.

Needle 80, shown in FIG. 10, is constructed in accordance with the principles of the present invention to engage and electrically couple to electrical contacts 55 of electrical access port 38. Needle 80 preferably has solid tip 81 including beveled end 82 for smoothly traversing tissue. Needle 80 has a plurality of circumferential electrical contacts 83 separated by insulators 84. Electrical contacts 83 mate with respective ones of the plurality of electrical contacts 55 disposed within electrical access port 38. Needle 80 is inserted externally through the skin and into chamber 50 until end 82 contacts the bottom of the chamber. Needle 80 preferably has a gauge of 20, 21, or 22, although other gauges can be used with the present invention. It is expected that there will be twice the number of electrical contacts 83 as there are ultrasonic elements mounted on sheath 22.

Electrical contacts 83 preferably are about 0.5 mm wide, and separated by insulators between about 0.5 mm and about 1.0 mm wide, so as to mate with electrical contacts 55 of electrical access port 38. Accordingly, electrical contacts 83 shown in FIG. 10 occupy about 3.5 mm along the length of the needle. In this embodiment, tip 82 is about 2.5 mm long, so that the tip and electrical contacts occupy about 6.0 mm of the length of needle 80.

Needle 80 preferably includes hollow core 85 through which passes insulated conducting elements 86, e.g., wires or thin metal strips. Each one of electrical contacts 82 preferably is connected to a conducting element. Conducting elements 86 join to appropriate secondary contacts (not shown) at the end of the needle 80. These secondary contacts are plugged into an appropriate counterpart on the end of a cable to connect the ultrasonic elements to suitable circuitry 120 for driving the ultrasonic elements. Circuitry 120, which is per se known, is connected to conventional processing circuitry for converting the signals received from the ultrasonic elements into output representing the flow of blood through graft 21.

In an alternative embodiment (not shown), the access ports may be omitted, and the connecting lumen may be brought out through the skin for temporary (e.g., approximately one week or less) monitoring and flow adjustment. Such an embodiment is desirable when short term adjustments are anticipated, and for use with animal subjects that will be euthanized for examination. Alternatively, after appropriate preparation of the skin and connecting lumen, the connecting lumen may be cut at the skin level and the remaining length of the connecting lumen allowed to retract under the skin. This latter technique is currently clinically accepted practice for handling temporary epicardial pacing wires placed during cardiac surgery.

For purposes of illustration, an example of the methods in accordance with the present invention is now given. First, graft 21, sheath 22, balloon 23, connecting lumen 24 and dual access port 40 described herein above with respect to FIG. 1 are implanted within a patient. When the physician desires to change the flow of blood through the graft 21, the patient first is connected to EKG and oxygen saturation monitors, and has temporary IV access established. The skin of the patient then is pierced with needle 80 and, it is directed through septum 52 of the electrical access port portion of dual access port 40 until it is seated within chamber 50. This establishes an electrical connection between ultrasound elements 32 and 33 and circuitries 120 and 130. Ultrasound signal processor circuitries 120 and 130 than confirm a good signal representing the flow of blood through graft 21.

The physician then punctures the skin with needle 101, directing it through septum 44 of the balloon access port portion of dual access port 40. The physician then infuses or withdraws a small amount of inflation medium using infusion device 100 to inflate or deflate, respectively, balloon 23, thereby changing the degree of constriction of graft 21 and altering blood flow through the graft.

The physician carefully monitors the flow signals as well as vital signs and oxygen saturation as the balloon is inflated to establish a desired flow level. The patient is then observed for about 10 minutes for stability, after which the two needles are withdrawn from the skin. The patient is then observed for another short interval, e.g., about 10 minutes, prior to termination of the procedure. Advantageously, the foregoing procedure does not have to be performed in an operating room, but can be readily performed in an intensive care unit or a cardiac catheterization facility.

Figure 11:
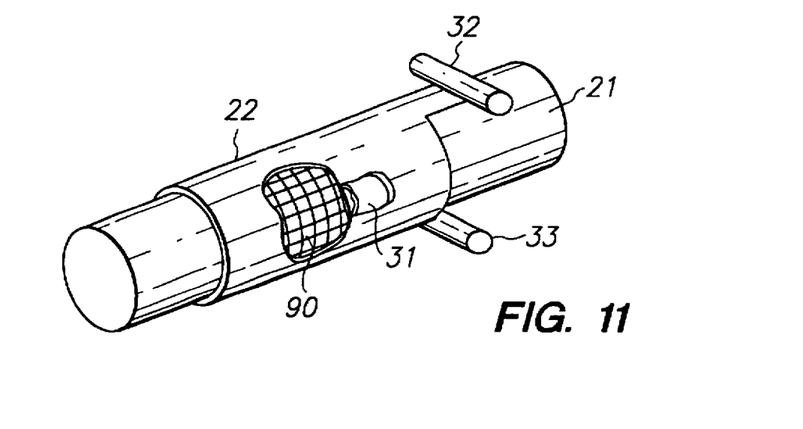
FIG. 11 is a perspective view, partly cut-away, of an alternative embodiment of the graft of FIG. 1.
Figure 12:
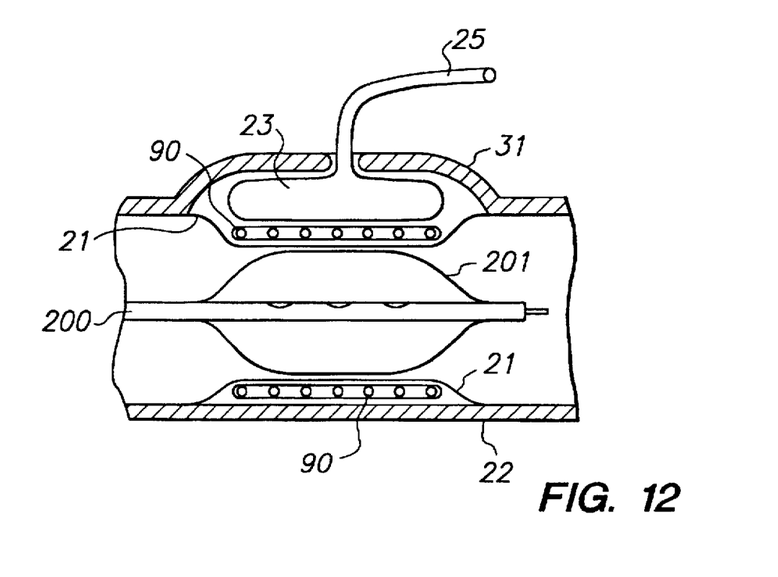
FIG. 12 is a fragmentary sectional view illustrating a step of re-expanding the graft of FIG. 11 using a balloon dilatation catheter.

Referring now to FIGS. 11 and 12, a further alternative embodiment of the present invention is described. In FIG. 11, balloon 23 is omitted from raised tube portion 31 of sheath 22 for clarity. In this embodiment, plastically deformable member 90 is inserted between balloon 23 and graft 21. Deformable member 90 is preferably a cylinder formed by wrapping a wire mesh around graft 21. When balloon 23 is inflated, it plastically deforms deformable member 90 onto graft 21, constricting the cross-section of graft 21 and altering its flow characteristics. Because deformable member 90 is plastically deformed by the inflation of balloon 23, it resists re-expansion due to hydraulic forces within graft 21 once balloon 23 is deflated. Thus, balloon 23, connecting lumen 25 and balloon access port 24 need not be capable of sustaining high pressures for prolonged periods, but only for the relatively short intervals required to deform deformable member 90. Deformable member 90 may, for example, plastically deform between about 0.5 mm and about 5.0 mm in a direction perpendicular to the longitudinal axis of the graft.

As shown in FIG. 12, re-expansion of graft 21 after reduction in the cross-section of deformable member 90 may be accomplished using a conventional balloon dilatation catheter 200 in accordance with well-known percutaneous catheterization techniques. Thus, expansion of the balloon 201 of balloon catheter 200 within graft 21 deforms deformable member 90 to an expanded diameter, thus increasing flow through graft 21. Again, because deformable member 90 is plastically deformed by the dilatation catheter, the graft will retain its enlarged cross-section after the balloon dilatation catheter is withdrawn. The clinical situation in which this deformable stent may be advantageous includes all cases where it is anticipated that eventual occlusion of the graft will be desired, such as pulmonary atresia where there is an intact ventricular septum, and with Fontan fenestrations.

The present invention provides significant advantages over previously known methods of treating children with a variety of complex congenital heart diseases. However, it is not limited to treatment of children with congenital cardiac disease. It can be applied to any graft or native vessel in which measurement and adjustment of blood flow, either chronically or acutely in humans or non-humans, is desired.

As also will be apparent to one of skill in the art, balloon access port 24 and electrical access port 38 may be used individually in numerous applications other than those involving grafts. In particular, the ability to establish a hydraulic (or pneumatic) coupling to an implantable device, or multiple electrical connections to a subcutaneously implanted access port using a single needle stick, provide significant benefits compared to previously known techniques. The balloon access port and electrical access port and needle of the present invention increase the practicality of a number of diagnostic and therapeutic techniques relying on implantable devices.

The balloon access port and inflation apparatus of the present invention may be advantageously used in any application where it is desirable to hydraulically or pneumatically activate an implantable device using a subcutaneously implantable access port.

Examples of applications for the electrical access port of the present invention include the general category of biosensors, such as ion-sensitive field effect transistors ("ISFETS" and "CHEMFETS") used for monitoring electrolytes (such as potassium), glucose and pH, clinical applications such as monitoring blood glucose in diabetics, serum potassium in patients with cardiac disease taking multiple diuretics, other electrolytes in renal failure patients, and vaginal pH. Yet other applications include intermittent hemodynamic monitoring using ultrasound technology, such as permanent continuous hemodynamic monitoring of ventricular function indices in patients with severe heart failure.

Additionally, direct assessment of central or peripheral neuronal function using electrical sensors and stimulators have been proposed and may be obtained using the electrical access apparatus and methods of the present invention. Further, powering and monitoring the function of pacemakers, implanted cardioverters/defibrillators, and artificial hearts may constitute other important applications of the present invention.

Those skilled in the art will appreciate that the invention can be practiced in other than the described embodiments, which are presented for purposes of illustration and not of limitation.

What is claimed is:

1. Apparatus for adjusting blood flow within a vascular graft, the vascular graft being formed of a compliant material having an exterior surface and a cross-section, the apparatus comprising:
   a balloon disposed against the exterior surface of the vascular graft;
   a sheath disposed around the balloon and the vascular graft, the sheath being substantially less compliant than the vascular graft, the sheath having a portion forming an aperture adjacent to the balloon;
   a first subcutaneously implantable access port; and
   a substantially non-distendable lumen disposed through the aperture in the sheath to provide fluid communication between the balloon and the first subcutaneously implantable access port;
   wherein inflation of the balloon to constrict the vascular graft causes substantially no crimping or infolding of the compliant material.

2. The apparatus as defined in claim 1 further comprising:
   first and second piezoelectric elements disposed on the sheath in opposition across the cross-section of the vascular graft;
   a second subcutaneously implantable access port; and
   means for electrically coupling the first and second piezoelectric elements to the second subcutaneously implantable access port.

3. The apparatus as defined in claim 1 further comprising:
   a first needle, the first needle in fluid communication with a source of inflation medium, the first needle engaging the first implantable subcutaneously implantable access port to inject the inflation medium into the first subcutaneously implantable access port.

4. The apparatus as defined in claim 3 further comprising an infusion device for metering the inflation medium injected into the first subcutaneously implantable access port.

5. The apparatus as defined in claim 4 wherein the infusion device comprises:
   a bore in fluid communication with the first needle and a pressure sensing port;
   a plunger mounted in the bore;
   means for depressing and retracting the plunger to control the amount of inflation medium injected into the first subcutaneously implantable access port.

6. The apparatus as defined in claim 2 wherein the first subcutaneously implantable access port and the second subcutaneously implantable access port comprise a dual access port.

* * * * *

UNITED STATES PATENT AND TRADEMARK OFFICE
CERTIFICATE OF CORRECTION

PATENT NO.  : 5,797,879
DATED       : August 25, 1998
INVENTOR(S) : William M. DeCampli It is certified that error appears in the above-identified patent and that said Letters Patent is hereby corrected as shown below:

<u>Column 16,</u>
Line 29, after "port", insert --

7. The apparatus as defined in claim 2 wherein the second subcutaneously implantable access port comprises a first plurality of electrical contacts, the apparatus further comprising:
   a second needle having at second plurality of electrical contacts adapted for coupling to respective one of the first plurality of electrical contacts;
   ultrasound circuitry for causing the first and second piezoelectric elements to emit and receive ultrasound signals, the ultrasound circuitry sensing the ultrasound signals emitted and received by the first and second piezoelectric elements to generate data signals;
   processing circuitry coupled to the ultrasound circuitry for computing a flow rate through the vascular graft from the data signals; and
   means for electrically coupling the ultrasound circuitry to the second plurality of electrical contacts.

8. The apparatus as defined in claim 1 wherein the first subcutaneously implantable access port comprises:
   a body defining a chamber and first and second apertures, the first aperture coupled to and in fluid communication with the substantially non-distensible lumen; and
   a septum extending across the second aperture.

9. The apparatus as defined in claim 2 wherein the second subcutaneously implantable access port comprises:
   a body defining a chamber and a first aperture, the first plurality of electrical contacts disposed within the chamber and electrically coupled to the first and second piezoelectric elements; and
   a septum extending across the first aperture --.

10. The apparatus infusion device of claim 5 further comprising a pressure transducer coupled to the pressure sensing port to monitor the pressure within the bore.

Line 30, replace "6" with -- 10 --.

UNITED STATES PATENT AND TRADEMARK OFFICE
CERTIFICATE OF CORRECTION

PATENT NO. : 5,797,879
DATED : August 25, 1998
INVENTOR(S) : William M. DeCampli It is certified that error appears in the above-identified patent and that said Letters Patent is hereby corrected as shown below:

Line 33, after "port", insert --

11. The apparatus as defined in claim 9 wherein each one of the first plurality of electrical contacts comprises a resilient member.

12. The apparatus as defined in claim 9 wherein the second needle comprises a cylindrical body and a non-coring tip adapted for smooth traversing of tissue, the second plurality of electrical contacts disposed on the cylindrical body of the second needle and adapted to electrically couple to respective ones of the first plurality of electrical contacts disposed within the chamber of the second subcutaneously implantable access port.

13. The apparatus as defined in claim 1 wherein the sheath includes a raised, tube-like portion that contains the balloon when the balloon is deflated.

14. The apparatus as defined in claim 1 further comprising a first and second piezoelectric elements disposed in first and second compartments, respectively, affixed to the sheath, the first compartment disposed from a longitudinally extended portion of the sheath.

15. The apparatus as defined in claim 14 wherein the vascular graft has a longitudinal axis and the piezoelectric elements are disposed across the cross-section of the vascular graft along a plane forming an angle of about 60° with the longitudinal axis of the vascular graft.

16. The apparatus as defined in claim 1 wherein the sheath comprises two half-circumferences and means for joining the two half-circumferences together.

17. The apparatus as defined in claim 1 wherein the vascular graft is pre-assembled with the balloon and sheath.

18. The apparatus as defined in claim 1 further comprising an elastically deformable tube surrounding a portion of the exterior of the vascular graft and disposed between the balloon and the vascular graft, so that when the balloon is inflated, the balloon causes the elastically deformable tube to become deformed and constrict the cross-section of the vascular graft.

UNITED STATES PATENT AND TRADEMARK OFFICE
CERTIFICATE OF CORRECTION

PATENT NO. : 5,797,879
DATED : August 25, 1998
INVENTOR(S) : William M. DeCampli Page 3 of 3

It is certified that error appears in the above-identified patent and that said Letters Patent is hereby corrected as shown below:

19. The apparatus as defined in claim 1 further comprising a plastically deformable tube surrounding a portion of the exterior of the vascular graft and disposed between the balloon and the vascular graft, so that when the balloon is inflated, the balloon causes the plastically deformable tube to become deformed and constrict the cross-section of the vascular graft, the plastically deformable tube retaining its deformed shape when the balloon is deflated. --.

Signed and Sealed this

Thirteenth Day of November, 2001

Attest:

*Attesting Officer*

NICHOLAS P. GODICI
*Acting Director of the United States Patent and Trademark Office*